United States Patent
Coles et al.

(10) Patent No.: US 6,733,482 B1
(45) Date of Patent: May 11, 2004

(54) FAECAL COLLECTOR HAVING BREATHABLE SKIN ATTACHMENT MEANS

(75) Inventors: Peter Coles, Chieti (IT); Olindo Evangelista, Chieti (IT); Fabio Cinelli, Bologna (IT); Eva Susanne Dominique Thurnay, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/958,393

(22) PCT Filed: Jun. 26, 1998

(86) PCT No.: PCT/US98/13298

§ 371 (c)(1),
(2), (4) Date: May 1, 2001

(87) PCT Pub. No.: WO00/00126

PCT Pub. Date: Jan. 6, 2000

(51) Int. Cl.[7] .................................................. A61F 5/44
(52) U.S. Cl. ...................................................... 604/355
(58) Field of Search ................................ 604/277, 332, 604/336, 337, 338, 339, 341, 342, 344, 355

(56) References Cited

U.S. PATENT DOCUMENTS

| | | | | |
|---|---|---|---|---|
| 2,524,750 A | * | 10/1950 | Bellinger | 604/334 |
| 3,444,788 A | * | 5/1969 | Sneen | 92/120 |
| 3,672,370 A | * | 6/1972 | Marsan | 604/277 |
| 3,695,268 A | * | 10/1972 | Marsan | 604/341 |
| 3,837,342 A | * | 9/1974 | Mitsuo | 604/344 |
| 4,233,977 A | * | 11/1980 | Mattson | 604/335 |
| 4,705,512 A | * | 11/1987 | Faucher | 604/332 |
| 4,917,691 A | * | 4/1990 | Briggs | 604/339 |
| 5,026,362 A | * | 6/1991 | Willett | 604/345 |
| 5,135,519 A | * | 8/1992 | Helmer | 604/332 |
| 5,248,308 A | * | 9/1993 | von Emster | 604/337 |
| 5,607,412 A | * | 3/1997 | Brown | 604/332 |
| 5,800,415 A | * | 9/1998 | Olsen | 604/336 |
| 6,407,308 B1 | * | 6/2002 | Roe et al. | 604/361 |
| 6,464,674 B1 | * | 10/2002 | Palumbo et al. | 604/385.01 |
| 6,641,569 B1 | * | 11/2003 | Coles et al. | 604/385.19 |

* cited by examiner

Primary Examiner—Weilun Lo
Assistant Examiner—Michael Bogart
(74) Attorney, Agent, or Firm—Larry L. Huston; Leonard W. Lewis; Steven W. Miller (57) ABSTRACT

A faecal management device has a bag and a flange. The faecal management device is placed on a wearer, in combination with an applicator. The applicator is configured to exert pressure from at least two spaced apart pressure points onto the flange of the device. The device is placed on a wearer by using placement lobes associated with the flange.

1 Claim, 8 Drawing Sheets

Fig. 7

FAECAL COLLECTOR HAVING BREATHABLE SKIN ATTACHMENT MEANS

FIELD OF THE INVENTION

The present invention relates to a faecal management device for babies, children or adults to be attached to the perianal area of the wearer. More particularly it relates to an applicator for such a device, which can be used to place the device in the perianal area of a wearer.

BACKGROUND OF THE INVENTION

Faecal management devices are known articles of manufacture that are designed to be worn principally by incontinence sufferers and in particular by bedridden patients. Such faecal management devices are attached to the perianal area of the wearer and are intended to entrap and immediately contain faecal material and other bodily discharges.

Such devices as they are mostly known today are constituted of a relatively long and narrow tube, at one extremity of which is positioned the aperture and the attachment device, which can be adhesive. Such bags are disclosed in, e.g. U.S. Pat. No. 3,577,989.

A problem naturally associated with these devices is their attachment to the human body. The approach which is mostly used in the field is to provide the device with an adhesive flange, which will stick to the perianal area.

U.S. Pat. Nos. 3,522,807 and 3,734,096 disclose faecal receptacles having an adhesive flange surrounding the aperture in the device, for attachment to the body of the patient in nursing or medical applications; said flange contains a plurality of tabs extending outwardly from the aperture and said tabs are covered with adhesive in the same manner as the rest of the flange and thus are designed to serve as adhering aids, and must be covered by a release means before use of the receptacles.

In GB-A-2,116,849, it was attempted to provide an adhesive faecal incontinence device which, among other properties, was easier to put in place on the patient. The solution brought up by GB-A-2,116,849 is, however, quite complex, involving individually removable sections of the release layer covering the adhesive layer on the flange surrounding the aperture, said sections having to be removed in a predetermined sequence in order to ensure optimum adherence.

Besides and in connection with optimum adherence, the correct placement of the device is also a key issue in the field of faecal management devices. Total or substantial misplacement of the device will lead to a severe misfunctioning, in particular incomplete collection of faeces and leakage in leakage. If the aperture of the faecal management device is not sufficiently in registry with the anal opening, substantial pressure, in particular on the flanges of the device, can build up in the defecation process. Such substantial pressure can lead to the detachment of the adhesively secured device, obviously entailing the most unwanted consequences.

If the misplacement of the device is recognised before use, the placement of the device is normally corrected, typically by the carer. The necessary detachment and reattachment of the device causes an additional stress on the affected areas of skin of the wearer. Many wearers, who make use of faecal management devices have a sensitive skin due to their age, whether very old or very young, and furthermore sometimes also suffer from skin irritations. Proper placement of the device in the first place is therefore highly desirable.

The faecal management devices which are disclosed in the mentioned prior art are normally handled and placed onto the skin of the wearer by using the flange itself. Typically, one of the first necessary handling steps is the removal of the release paper from the adhesive surface of the flange. When then placing the device, the caretaker will normally touch the adhesive area of the flange with the fingers and leave finger marks. Such marks will reduce the adhesive force of the affected areas of the adhesive surface, if dirt is deposited from the fingers or if an adhesive is used, which tends to adhere less on second contact with a surface.

Furthermore, during application of the faecal management device to the wearer by holding the flange, pressure typically needs to be exercised upon the flange. However, as a result of such pressure the flange may suffer deformation, leading to a poorer performance of the device, in particular to a poorer adhesion, discomfort or possibly leaking of the device.

In Kokai Patent Application No. HEI8 (1996) 117 261, an external accessory is described to assist in the placement of the adhesive part of the disclosed diaper onto the wearer. Such a tool may help in the placement of such an incontinence product when compared to the placement without any aide. However, the successful use of such a tool will require training, in particular if the tool is not specifically designed for its purpose. A further problem with such a tool is that a caretaker, for example, when dealing with a bedridden patient, may have only one hand available for the application of the device.

Hence, there still exists a need for faecal management devices which can be easily and correctly positioned onto the desired area of the wearer by the caretaker or wearer themselves without causing discomfort to the wearer or damage to the device.

In attempting to overcome all the aforementioned problems relating to the prior art, it has now been found that a specifically designed applicator which can be utilised with adhesive faecal management devices greatly facilitates the correct placement of the device. Furthermore such an applicator maintains the bag of the device in a folded configuration prior to the use of the device and supports the hygienic and protective packaging of the device.

SUMMARY OF THE INVENTION

The present invention relates to a faecal management device (10) comprising a bag (11), said bag (11) having an aperture (21) and a flange (12) surrounding said aperture for adhesive attachment to perianal area of wearer. More particularly, the invention relates to an applicator (40) for the placement of such a device (10) to the perianal area of a wearer. Claimed and described is an applicator (40), comprising a handling portion (42); characterised in that said applicator (40) comprises at least two pressure points (42).

BRIEF DESCRIPTION OF THE DRAWINGS

It is believed that the invention will be better understood from the foregoing description in conjunction with the accompanying drawings in which.

DETAILED DESCRIPTION OF THE INVENTION

Figure 1:
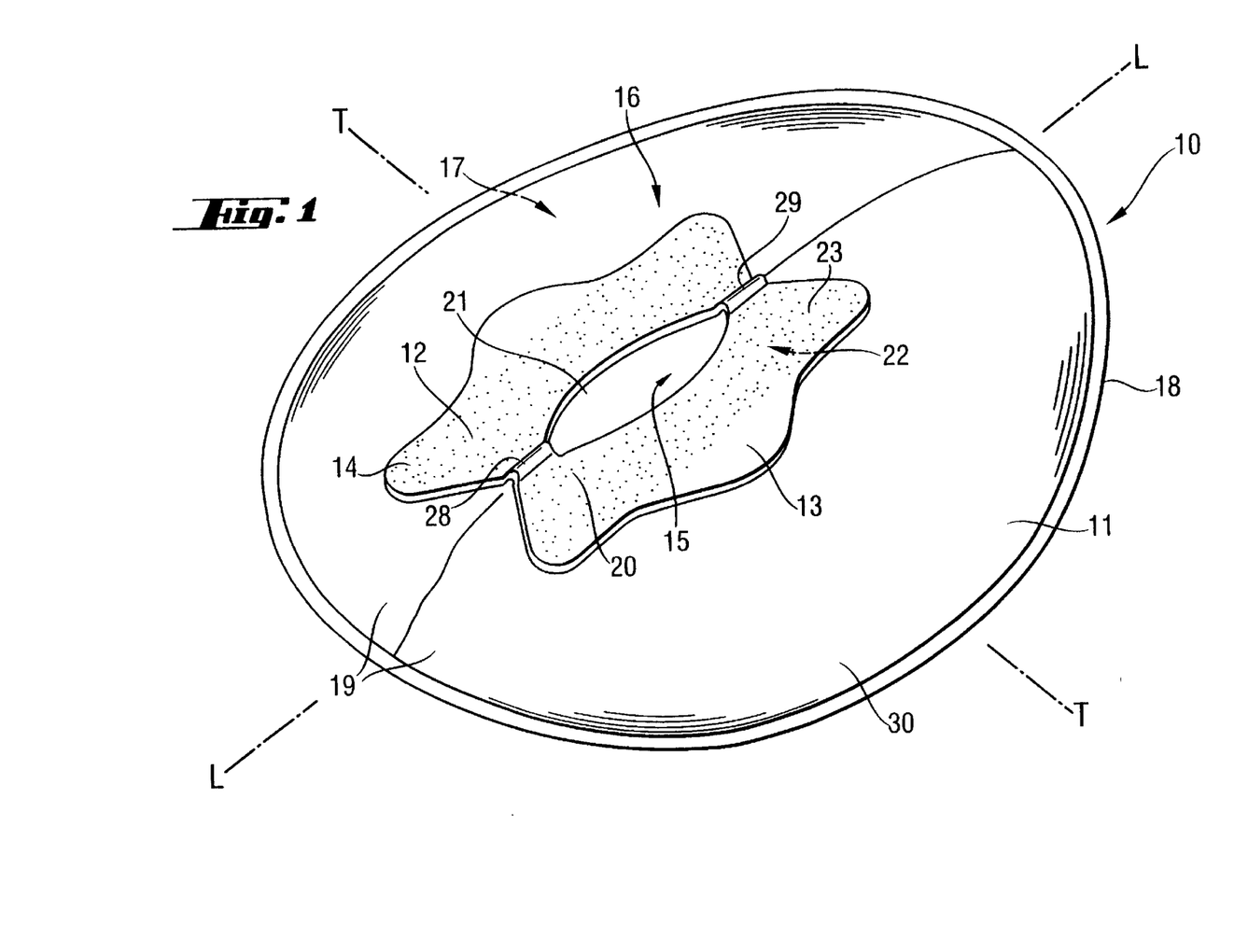
FIG. 1 is a perspective view of a preferred embodiment of a faecal management device.

The invention relates to a faecal management device (10) as shown in FIG. 1. The device (10) comprises a bag (11) and a flange (12).

Description of the Faecal Management Device as a Whole

Typically faecal management devices comprise a bag (11) having an aperture (21) and a flange (12) surrounding the aperture for preferably adhesive attachment to the perianal area of a wearer as visible from FIG. 1. Any faecal management device known in the art can be provided according to the present invention.

The bag (11) as used herein is a flexible receptacle for the containment of excreted faecal matter. The bag (11) can be provided in any shape or size depending on the intended use thereof, i.e. whether the device is intended for bedridden patients or active patients suffering from incontinence or requiring an artificial bowel or for infants. For example, elongated bags which are principally tubular or rectangular are typically utilised by bedridden patients and elderly incontinence sufferers. For more active wearers whether infants or adults, the faecal management device should preferably be anatomically shaped such that the device follows the contours of the body and can be worn inconspicuously by the wearer under normal garments.

Particularly, preferred shapes are flat circular type bags, cone shaped bags, truncated cone shaped bags and pyramidal or truncated pyramidal bags. In a most preferred embodiment of the present invention, the bag (11) has a substantially truncated cone shape. Typically the bags will have a wearer facing portion (16) and a garment facing portion (17). The wearer facing portion (16) of the faecal management device (10) is disposed adjacent the buttocks of the wearer. As such, the wearer facing portion (16) amply covers the buttocks of the wearer and does not hang between the thighs of the wearer.

In addition, the bag (11) is preferably shaped to allow at least partial insertion and retention of the bag in-between the buttocks of the wearer and thereby ensure good contact between the flange and the skin of the wearer. For example, the bag (11) may be provided with a neck portion or conduit.

The bag (11) is preferably designed to provide sufficient volume for faecal material under a variety of wearing conditions, also when worn by a freely moving, i.e. not bedridden wearer. Sitting on the bag, for example, will result in a largely reduced volume in some areas of the bag. Thus, the bag is preferably shaped to provide sufficient volume in areas which are not subjected to much pressure in wearing conditions such as sitting.

The bag (11) is designed to safely contain any entrapped material, typically it will be liquid impermeable, yet it may be breathable. The bag (11) is designed of sufficient strength to withstand rupture in use, also when pressure on the bag (11) is exerted in typical wearing conditions, such as sitting.

According to the present invention, depending on the shape of the bag (11) required, the bag (11) may be provided from a unitary piece of material or from a number of separate pieces of material, which may be identical or different and which are sealed at their respective peripheries.

In one preferred embodiment the bags herein have a wearer facing portion (16) and a garment facing portion (17) which comprise separate pieces of material. The wearer facing portion (16) and the garment facing portion (17) are sealed at the periphery of the bag (11), thus creating a bag peripheral rim (18). As is visible from FIG. 1, the wearer facing portion (16) of the bag (11) may comprise two further sections (19), which are secured to each other by means known to the man skilled in the art, such as adhesive, thermobonding or pressure bonding in order to provide the desired bag configuration. Said rim (18) may also be inside the bag, thus being coextensive with the inner surface (15) of the bag (11) rather than with the outer surface (30) of the bag (11). Preferably the bag (11) is asymmetrical to the transversal axis, so that the distance measured in the longitudinal direction from the centre of the aperture (21) to the front end of the bag (11) is shorter than the distance measured to the rear end of the bag (11).

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film and two non-woven layers. In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner surface (15) of the bag (11). Any known techniques for securing absorbent material to nonwoven and film substrates may be used to secure the absorbent material to the inner surface (15) of the bag. The absorbent material may also be arranged to have any desired shape or configuration (e.g., rectangular, oval, circular, etc.).

As shown in FIG. 1 the bag (11) is provided with an aperture (21) whereby faecal matter is received from the body prior to storage within the bag cavity.

The aperture (21) is surrounded by a flange (12) and may be provided in any shape or size, such as circular, oblong, heart shaped and may be symmetrical or asymmetrical, preferably the aperture has an oblong configuration either in the longitudinal or in the transversal direction or in both directions, e.g. the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering faecal matter.

The flange may be provided in any size depending on the wearer group for which the device is intended. Similarly the flange may be provided in any shape and preferably has a symmetrical shape preferably comprising a plurality of lobes (13)/(14).

The flange comprises a garment facing portion (22) and a wearer facing portion (23). In an preferred embodiment these are two large, substantially flat surfaces, however, the flange (12) may also comprise projections, a front projection (28) and/or a rear projection (29), designed to fit the perineal and/or coccygeal area of the wearer.

The flange (12) should be made of soft, flexible and malleable material to allow easy placement of the flange (12) to the perianal area. Typical materials include non-woven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimeters and a density of 5 to 250 $g/m^2$, more preferably 50 $g/m^2$. Other thermoplastic foam materials, or other suitable plastics sheet materials having the described properties of such foams (i.e., softness, pliability, stretchability, and contractability) might also be used. Preferably, the material of garment facing portion (22) of the flange (12) may extend into the defined aperture area so as to form a skirt or flap of material which prevents unintentional adhesion of the surface edges of the flange (12) defining the aperture (21) to one another during use.

According to the present invention the faecal management device (10) further comprises an attachment means to secure the device to the wearer. Such means include straps and more preferably comprises a body-compatible pressure sensitive adhesive (20) applied to the wearer facing portion (23) of the flange (12).

The adhesive (20) is preferably covered with a release means (not shown) in order to protect the adhesive (20), such as siliconized paper. The adhesive (20) can cover the entire wearer facing portion (23) of the flange (12) or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing portion (23) of the flange (12), so as to provide lobes (13)/(14) on either side of the flange (12) which are non-adhesive and can thereby serve to facilitate placement and removal of the device whilst avoiding contact with the adhesive. These lobes (13)/(14) are however preferably also covered by the release means. Before application of the faecal management device (10) to the skin of the wearer, the release means if present is removed.

According to the present invention any medically approved water resistant pressure sensitive adhesive may be used to attach the device to the perianal area of the wearer, such as hydrocolloid adhesives and hydrogel adhesives. Particularly effective adhesives in providing the desired adhesive properties to secure the flange to the skin of the wearer at the sensitive perianal area, whilst allowing for relatively painless application and removal, are formed from crosslinking polymers with a plastisicer to form a 3-dimensional matrix.

The adhesive (20) can be applied to the wearer facing portion (23) of the flange (12) by any means known in the art such as slot coating, spiral, or bead application or printing. Typically the adhesive (20) is applied at a basis weight of from 20 $g/m^2$ to 2500 $g/m^2$, more preferably from 500 $g/m^2$ to 2000 $g/m^2$ most preferably from 700 $g/m^2$ to 1500 $g/m^2$ depending on the end use envisioned. For example, for faecal management devices (10) to be used for babies the amount of adhesive (20) may be less than for faecal management devices (10) designed for active adult incontinence sufferers.

Figure 2:
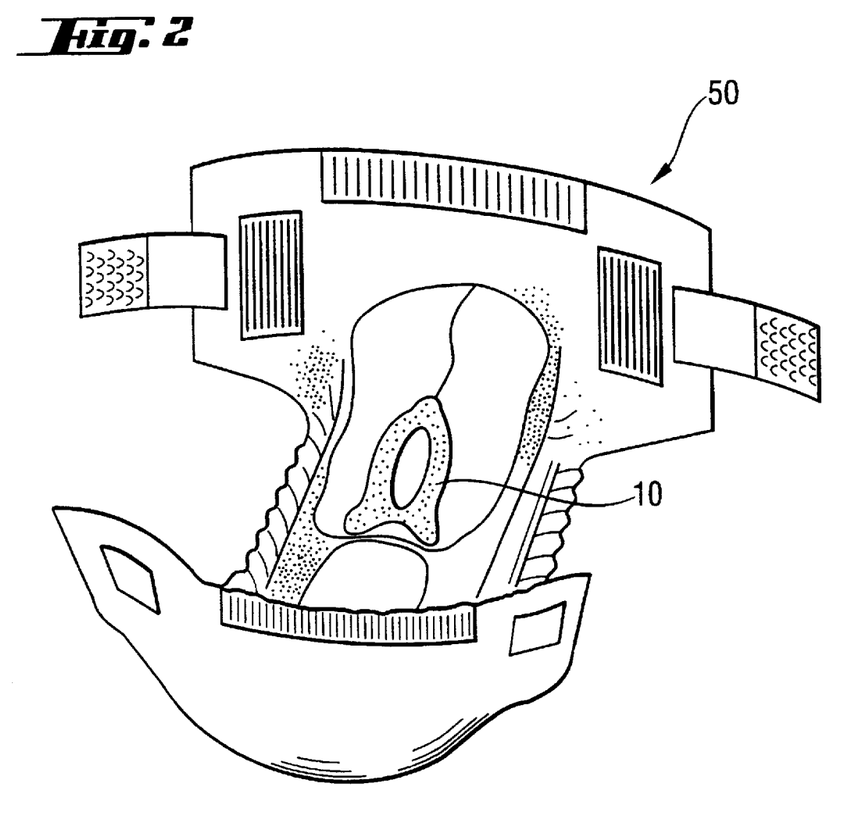
FIG. 2 is a perspective view of a diaper and a faecal management device, which can be worn in combination according to the present invention.

Detailed Description of a Diaper to be Worn in Combination with the Faecal Management Device The faecal management device (10) of the present invention has been found to be particularly useful and beneficial when used in conjunction with a garment, or diaper (50), preferably a disposable diaper—refer to FIG. 2. The faecal management device (10) is preferably first placed in the perianal area of the wearer before the disposable diaper (50) is applied. In particular, the diaper (50) is positioned over the faecal management device (10) and fastened in a conventional manner around the body of the wearer. It has been found that, in addition, to providing excellent separation between urine and faecal material, the combined faecal management device (10) and diaper (50) system actually reduces skin irritation, which may at times occur, especially since the group of typical wearers includes the very old, the very young and the unhealthy wearers.

In effect, the presence of the faecal management device (10) permits the formation of a separation layer between the skin of the wearer and the diaper (50), i.e. a part of the absorbent core (58) of the diaper (10). The diaper (50) can be of the conventional type (an embodiment of which is described below although not a limiting example by any means) or can be adapted to contain in an effective and comfortable manner the faecal management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
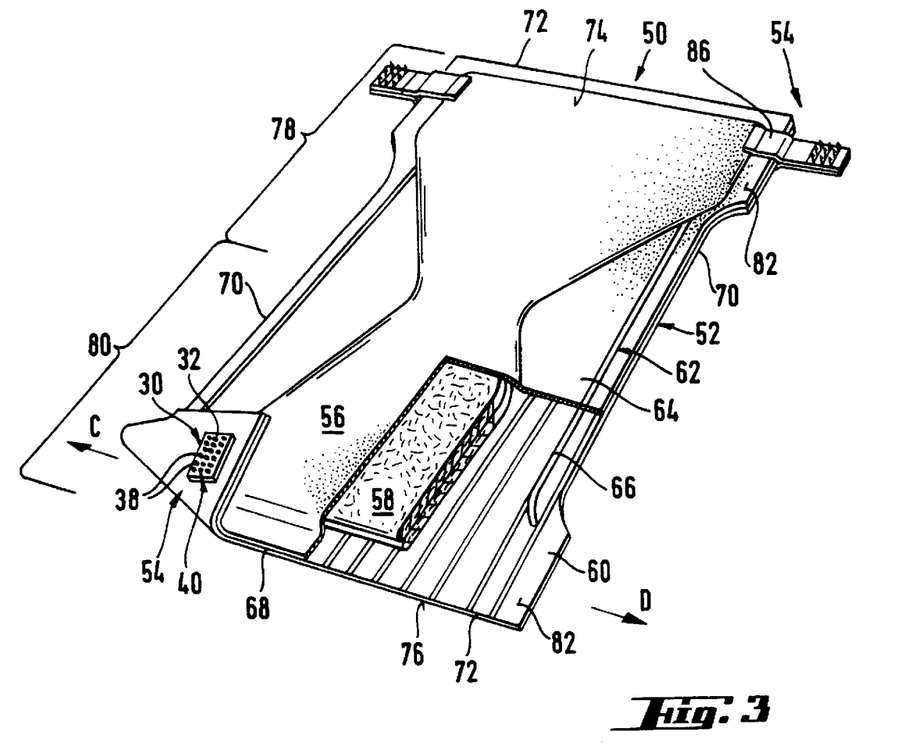
FIG. 3 is a partially cut-away perspective view of a diaper to be worn in combination with a faecal management device according to the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50) opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying caliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical Plas Tec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combination of natural and synthetic fibres. Preferably, it is made of a material that isolates the skin of the wearer from liquids retained in the absorbent core (58).

There are a number of manufacturing techniques which may be used to manufacture the topsheet (56). For example, the topsheet (56) may be a non-woven web of fibres. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

Detailed Description of the Applicator

To allow a more detailed and clear description of the present invention, in the following paragraphs firstly a number of terms, as used herein, will be defined.

Regarding the faecal management device (10) the longitudinal axis is to be understood as follows: The direction which is substantially defined by the anal groove in the intended wearing position shall define the longitudinal direction. The longitudinal axis is an axis in the longitudinal direction, which crosses the centre of the aperture (21). The most preferred indication of the intended wearing position is the presence of one or two projections (28) and/or (29) designed to fit the perineal or coccygeal area of the wearer, a less preferred indication of the intended wearing position is a fold in said flange (12) prior to use intended to be placed in parallel to the anal groove when placing the product. The longitudinal axis is typically also an axis of symmetry of the bag (11).

The transversal axis is an axis perpendicular to said longitudinal axis, which crosses the centre of the aperture (21). The bag (11) is typically not symmetrical to the transversal axis.

Longitudinal, when used for the applicator (40), shall denote the direction which is substantially parallel to the longitudinal direction of the faecal management device (10) when the applicator (40) is used for placing the device (10). Typically the pressure points (42) are aligned along a longitudinal axis.

The garment facing portion (17) is the portion of the bag (11), which is generally oriented away from the wearer, when the faecal management device (10) is worn, and towards a garment, if a garment is worn. The garment facing portion (17) does not comprise the aperture (21). The size and the shape of the garment facing portion (17), in particular its length and width, are defined by the bag peripheral rim (18). Sections of material comprised by the rim (18) or seal do not form part of the garment facing portion (17).

The wearer facing portion (16) is the portion of the bag (11), which comprises the aperture (21) and is generally oriented towards the wearer, when the faecal management device (10) is worn. The size and the shape of the wearer facing portion (16) are defined by the bag peripheral rim (18). Sections of material comprised by the rim (18) or seal do not form part of the wearer facing portion (16).

Centre is used to describe a point of an object or a part of an object, which coincides with the centre of mass, if said object or part were of uniform density.

Thus for the aperture (21), the centre is to be determined when the area within the contour of the aperture (21) is considered to be filled with a material of uniform thickness and density, when the flange (12) is unbent.

Unbent is used with regard to the flange (12). The flange (12) is typically bent along a longitudinal axis to place it onto the perianal area of the wearer. In an unbent state the flange (12) is typically flattest. Flat is used in the description of a three-dimensional object, such as the flange (12), if the object can be thought to be fully contained by a cuboid, characterised by three characterising lengths, of which one first length is less than half of either of the two other characterising lengths. If the object is flexible in shape, so that it may take several shapes without a substantial effect on its properties or damage, it is called flat if it is flat in one of said shapes. Such an flexible object is in its flattest shape if said first characterising length is minimal.

Figure 4:
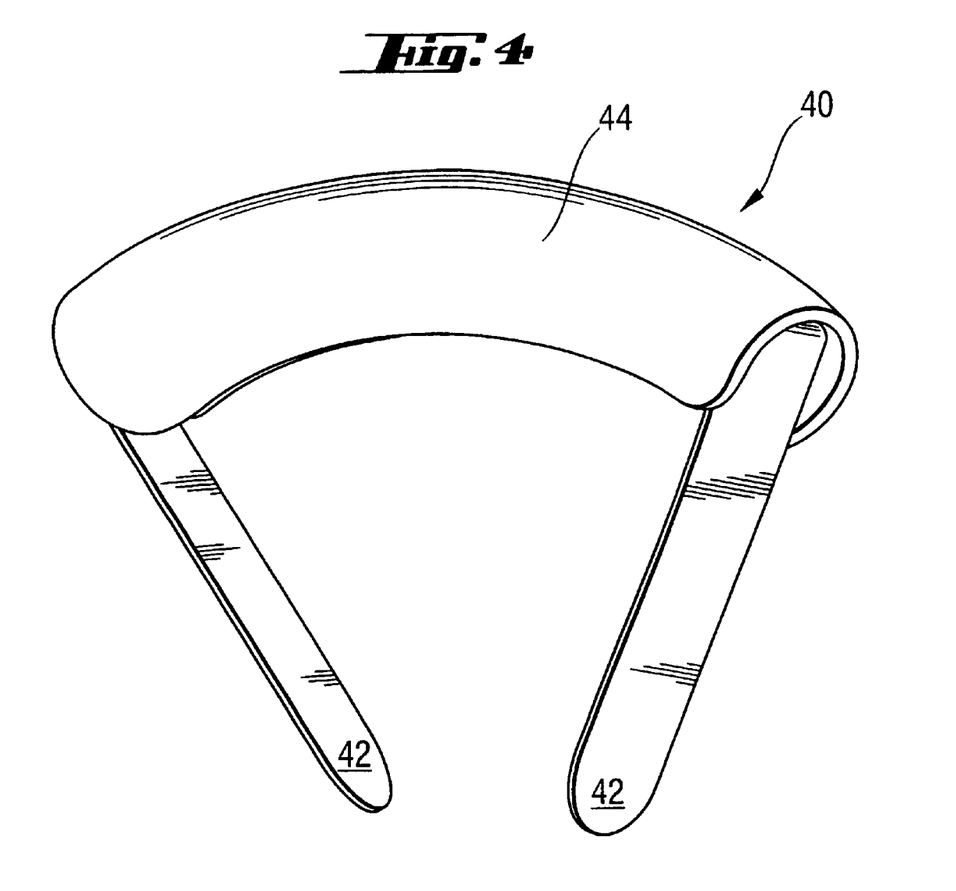
FIG. 4 is a schematic view of a first preferred embodiment of the applicator.
Figure 5:
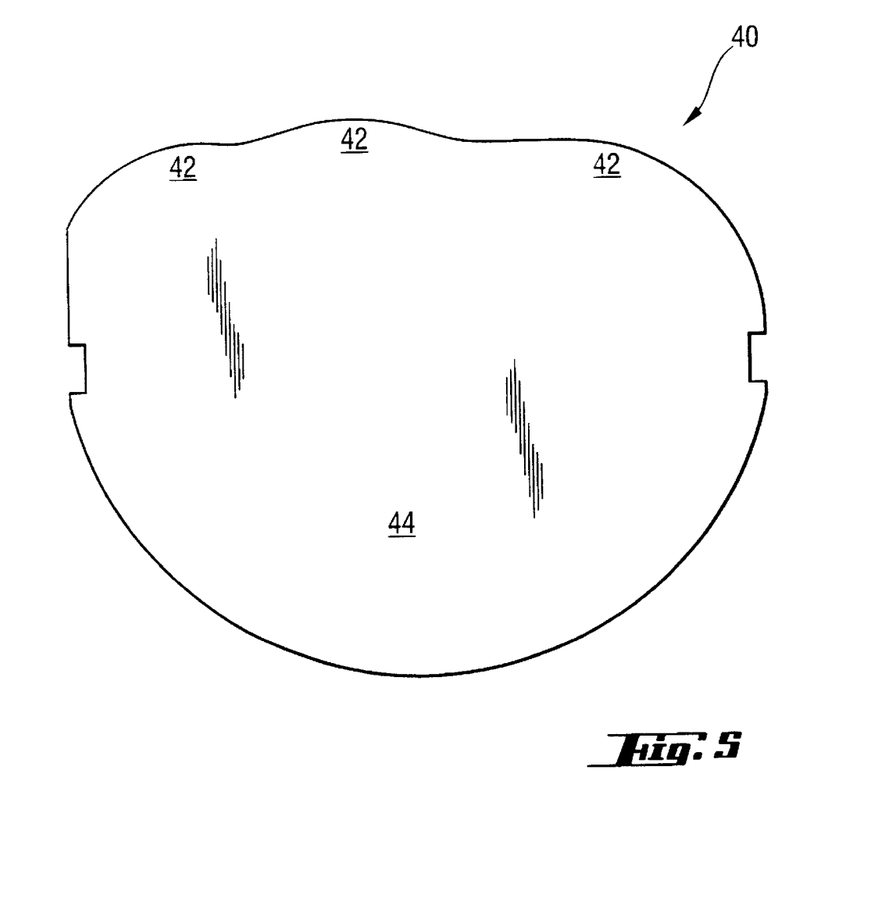
FIG. 5 is a schematic view of a second preferred embodiment of the applicator.
Figure 6:
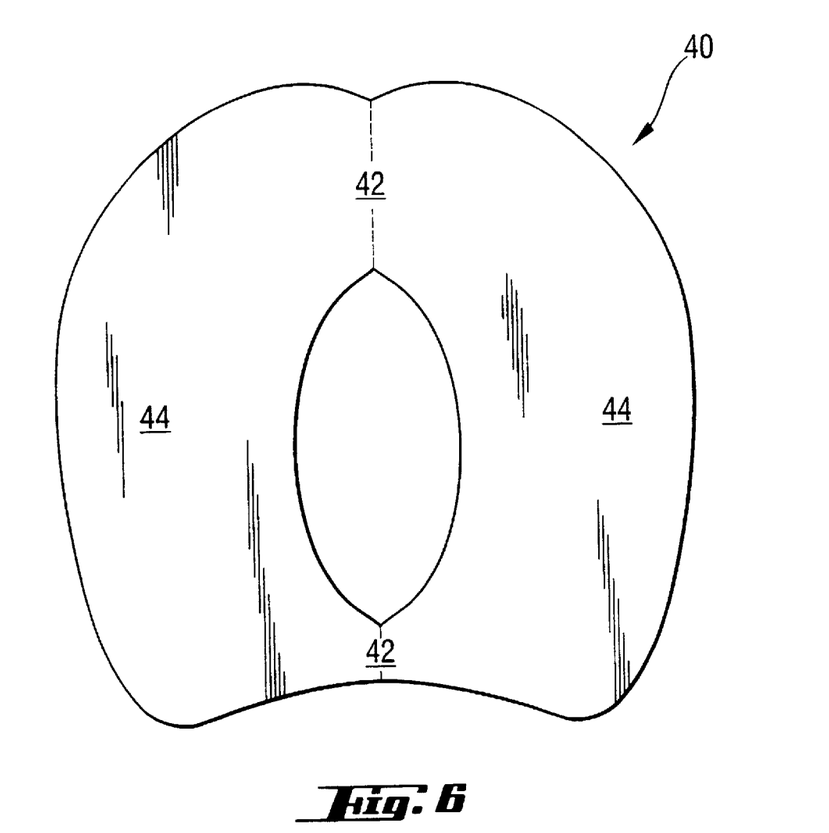
FIG. 6 is a schematic view of a third preferred embodiment of the applicator, which is unfolded.

The invention relates to an applicator (40) to be used for the placing of a faecal management device (10) to the perianal area of a wearer, preferred applicators (40) are shown in FIGS. 4 to 6.

Preferably the faecal management device (10), which is to be used in combination with the applicator (40), is provided with pressure sensitive adhesive (20) on the flange (12) for adhesive attachment to the skin in the perianal area of a wearer. For secure attachment of the device (10) pressure thus needs to be exerted onto the device and the skin of the wearer to ensure adhesion. While this can be done, for example through the bare hands and fingers, it has now been found that the use of an applicator allows the caretaker or wearer to exert more pressure and is of great help in ensuring that pressure is exerted in a controlled manner onto the correct areas.

In addition the utilisation of the applicator (40) also greatly assists in assuring that the bag (11), which is preferably provided in a folded configuration prior to the placing of the device (10), remains in that folded configuration during application. The applicator (40) was also found to provide hygienic and mechanical protection for the device (10). Furthermore the applicator (40) was found to assist in the economic, aesthetically pleasing and protective packaging of the faecal management device (10).

The applicator (40) according to the present invention is thus configured so as to exert pressure from at least two pressure points (42) preferably onto the flange (12) of the faecal management device (10). Such a configuration has been found beneficial for the secure attachment of a faecal management device (10) without causing pain to the wearer and without being particularly difficult or time consuming for the person placing the device (10).

In a preferred embodiment the applicator (40) exerts pressure onto two points, as easily seen in FIG. 4. Preferably these two pressure points (42) have a position and a distance chosen so as to exert pressure onto the perineal and the coccygeal area of a wearer, but more preferably not onto the sphincter muscle and the anus of a wearer. Their position thus largely depends on the intended wearer group and on the faecal management device (10) used in combination with the applicator (40). Preferred faecal management devices (10) are provided with one or two projections, a front projection (28) and/or a rear projection (29), designed to fit the perineal and/or coccygeal area of the wearer. These projections help in ensuring a good seal between the flange (12) and the body of the wearer and thus ensure the complete collection of faecal matter in the defecation process and prevent leaking of faecal material collected by the device (10). If such projections (28) and/or (29) are present, the applicator (40) for the device (10) is preferably provided with pressure points (42) which exert pressure onto these projections (28) and/or (29) by contacting the corresponding areas on the garment facing portion (17) of the flange (12).

Other preferred embodiments may have more than two pressure points (42). For example, it may be beneficial to exert pressure on said projections (28) and/or (29) and on other selected points, e.g. two additional points on the anal groove of the wearer (by having contact with the corresponding areas on the garment facing portion (17) of the flange (12)) to further improve the seal and fit of the flange (12) on the wearer.

In yet another preferred embodiment one of the pressure points (42), e.g. a central protrusion as depicted in FIG. 6, is positioned so as to exert pressure into the anus and is hereinafter referred to as a central pressure point (42). Preferably, such a central pressure point (42) is brought in registry with the aperture (21) of the faecal management device (10) before and/or whilst placing the device (10). This central pressure point (42) does not typically assist in pressing the adhesive (20) onto the skin of a wearer, but helps the wearer/caretaker to bring the aperture (21) in registry with the anus. It has been found that the presence of such a central pressure point (42) is particularly helpful in ensuring the correct placement of the device, since it allows the person placing the device to follow and feel the contours of the wearer's body by keeping said central pressure point (42) in contact with the wearer's body. Bringing said central pressure point (42) in registry with the anus of the wearer can then ensure the placing of the aperture (21) in registry with the wearer's anus, which is highly important for the correct functioning of a faecal management device (10).

If no such central pressure point (42) as described above is present, the other pressure points (42) are preferably positioned so that the two pressure points (42), which are closest to the anus of the wearer, when the device (10) is placed, are separated from one another by at least 1 cm, preferably by at least 3 cm, more preferably by at least 5 cm. If only two pressure points (42) are present on an applicator (40) intended for faecal management devices (10) for babies their distance is preferably 1 to 15 cm, more preferably 3 to 12 cm, more preferably 5 to 10 cm apart from one another. If one central pressure point (42) is present, it is preferably positioned centrally between the two pressure points (42), which are closest to the anus of the wearer, when the device (10) is placed. This central pressure point (42) does not need to be symmetrical to the neighbouring two pressure points (42), since in a preferred embodiment the device (10) itself is not symmetrical to the transversal axis: The distance measured in the longitudinal direction from the centre of the aperture (21) to the front end of the bag (11) is preferably shorter than the distance measured in the longitudinal direction from the centre of the aperture (21) to the rear end of the bag (11).

According to the present invention said pressure points (42) of the applicator (40) are to be understood as areas, which typically have a non-negligible size (as opposed to points in a narrow mathematical sense). The area is preferably not so small that damage is done to the faecal management device (10) or that pain is caused to the wearer. The area of the pressure points (42) is on the other hand preferably not too large regarding the anatomy of an intended wearer, so that the applicator (40) exerts pressure only in the perianal area of the wearer and preferably can be used in-between the buttocks of a wearer. Preferably the surface area of each of said pressure points (42) is independently from 0.01 mm$^2$ to 500 mm$^2$, more preferably from 0.1 mm$^2$ to 50 mm$^2$, however the area largely depends on the particular embodiment of the applicator (40) and the faecal management device (10) to be used in combination with the applicator (40).

The applicator (40) is typically used by a person, whether the wearer or a caretaker, and typically handled by that person using the hands. Thus, to be held and to be used to exert pressure by the caretaker or wearer, the applicator typically comprises a handling portion (44). This handling portion (44) may comprise separate pieces of material, as shown in FIG. 4, or may be an integral part of the applicator (40), as shown in FIGS. 5 and 6. Also, separate portions of the unfolded applicator (40) may form part of the handling portion (44) of the folded applicator (40), without these separate portions comprising separate pieces of material, as shown in FIG. 5.

The applicator (40) may further comprise various labels, e.g. colour labels. One such label can be used to indicate which portion of the applicator is to be brought in registry with a particular portion of the faecal management device (10). For example, a colour label may indicate which portion of the applicator (40) is to be brought in registry with the centre of the aperture (21). Such a colour label should preferably still be visible also when covered by the bag (11), in particular when covered only by one layer of the material of the bag (11). Thus, said colour label is typically visible through the aperture (21) when the applicator (40) is combined with the faecal management device (10) and indicates how to place the device (10) in registry with the anus of a wearer by using the applicator (40).

Similarly colour labels on the applicator (40) can be also used to indicate how the applicator in combination with the faecal management device (10) is to be oriented for placement, e.g. with regard to the perineal and the coccygeal areas of a wearer. Furthermore the applicator (40) can be labelled to provide usage instructions or any other written instructions.

An applicator (40) according to a present invention can be made in a variety of shapes and from a variety of materials. The applicator (40) may be made from one unitary piece of material or may comprise several pieces of material.

The applicator (40) for the faecal management device (10) can be made of any suitable material. The material should allow the transfer of the required forces from the handling portion (44) of the applicator (40) to the pressure points (42). Preferably the material is inexpensive and suitable for a mass manufacturing process. Preferably the material is environmentally friendly for disposal, in particular for flushing in a toilet.

Preferred materials are wood, metal, plastic and cardboard. Cardboard maybe be provided with a coating, e.g. a wax coating to improve the hygienic handling of the applicator (40) and to prevent any dirt from easily sticking to or otherwise soiling the applicator (40). Preferably the cardboard has a thickness from 0.01 to 5 mm, more preferably from 0.1 to 1 mm, most preferably from 0.3 to 0.7 mm.

Preferred materials also include those used for tampon applicators, which are typically provided from plastics, polymers or flushable smooth surfaced cardboard. Materials such as paper or wood pulp which are also used for tampon applicators are hence also within the scope of the present invention. More preferred materials are disclosed in EP 613672 A1, where a commercially effective and aesthetically-acceptable rapidly-disintegrating water-soluble disposable tampon applicator and a method for making it are disclosed. The materials disclosed in EP 613672 A1 such as water-soluble polymers having a coating comprising a water-insoluble polymeric material selected from the group consisting of wax (comprising natural wax and synthetic wax), hydrogenated vegetable oil, and food grade shellac, may also be utilised for the application herein. Among the preferred water-soluble polymers is polyvinyl alcohol and thermoplastic starch.

According to the present invention, the applicator (40) may be provided in numerous configurations having pressure points (42), which provide the benefits as described herein. A first preferred embodiment of the applicator (40), which is depicted in FIG. 4, comprises a handling portion (44) and two pegs. Preferably this embodiment is made from plastic material. The applicator is symmetrical to its longitudinal axis. The handling portion (44) is open towards the pegs, thus forming a cavity. The ends of the pegs pointing away from the handling portion (44) comprise the pressure points (42). The pegs comprise a base piece and are flexibly joined to the handling portion (44) by adhesive in contact with this base piece. This first embodiment of the applicator (40) when dimensioned to be used for a faecal management device (10) for a baby has the following lengths and widths: The pegs have a length of 4 cm and a width of 8 mm. The distance between the pegs measured at the handling portion (44) along a straight line is 9 cm. The pegs are flexible so that the distance between the pressure points (42) can be increased and so that the pegs can exert a force directed towards each other. When combined with a faecal management device (10) this force can be used to hold the applicator (40) and the device (10) together. The cavity of the handling portion (44) then assists in maintaining the bag (11) in a folded configuration, since parts of the bag (11) extend into that cavity.

A second preferred embodiment of the applicator (40) is depicted in FIG. 5 and is preferably made from cardboard. It comprises three pressure points (42). The applicator (40) also comprises two notches to hold a rubber band in place. When this embodiment of the applicator (40) is dimensioned to be used for a faecal management device (10) for a baby, the longitudinal length measured between the two notches is 12.5 cm, the longest width measured perpendicular to said length is 10.3 mm and the cardboard used has a thickness of 0.5 mm.

The third preferred embodiment of the applicator (40), which is depicted in FIG. 6, is also preferably made from cardboard. It comprises two pressure points (42). The applicator (40) comprises a central orifice and is folded to provide the handling portion (44) which enclose parts of the bag (11). The applicator is symmetrical to its longitudinal axis. When this embodiment of the applicator (40) is dimensioned to be used for a faecal management device (10) for a baby, the length measured along the longitudinal axis is 8.5 cm, the longest width measured perpendicular to said length is 13 mm. The cardboard used has a thickness of 0.5 mm. While this embodiment is not symmetrical to the transversal axis, a cardboard embodiment comprising an orifice, which is symmetrical to a transversal and to a longitudinal axis, is also a preferred embodiment.

In a preferred embodiment the faecal management device (10) is provided in a particular configuration prior to use. In that configuration, the flange (12) is folded along the longitudinal axis to allow easier placement of the flange (12) in-between the buttocks of a wearer. Furthermore the bag (11) is preferably folded, which provides numerous advantages. For example, folding of the bag (11) allows a smaller packaging format of the device (10), thus reducing the costs for transport and packaging material. Furthermore, the handling of the device (10) is more convenient if the bag (11) is folded, since e.g. the bag (11) may otherwise cover the placement lobes (13) or the handling portion (44) of the applicator (40). The bag (11), when not folded, may also cover parts of the body of the wearer, so that the person placing the device (10) cannot sufficiently visually control the placing.

Numerous patterns for the folding of the bag (11) are within the scope of the present invention. The folding should result in a sufficiently small size of the bag (11) in its folded state to provide the benefits described above, should not cause damage to the bag and should allow an uncomplicated unfolding of the bag after placement.

For example, the bag (11) may be folded in the following way: As a first step the bag (11) is folded (17) along two transversal lines, so that diametrically opposed portions of the rim (18) lie over the garment facing portion and preferably do overlap over a length of about 5 mm; as a second step the partially folded bag (11) is folded (17) along two longitudinal lines, so that diametrically opposed portions of the rim (18) lie over the garment facing portion and preferably do overlap over a length of about 5 mm; as a third step the partially folded bag (11) is folded (17) along the longitudinal axis so that diametrically opposed portions of the wearer facing portion (16) touch each other. Alternatively the folding steps described above as first step and second step can be carried out in inverted sequence, so that the bag (11) is first folded along two longitudinal lines.

Most preferably the applicator (40) and the faecal management device (10) in combination are provided in a particular configuration prior to use. This allows ready application of the faecal management device (10) with only a few handling steps, since there is no need to have separate items at hand (the applicator (40) and the device (10)) and to position the applicator on the appropriate areas of the faecal management device (10) for application.

The applicator (40) may be provided with a means to hold the applicator (40) and the faecal management device (10) together. This means will typically also ensure the correct positioning of the applicator (40) relative to the device (10) and help to maintain the folded configuration of the bag (11), if the bag is folded. Such a means preferably are provided in the form of any string or band, which may be provided in form of a closed loop, such as a rubber band. Such a means may also be provided in form of a clamp or a clip, made from any suitable material such as plastic or metal.

Figure 7:
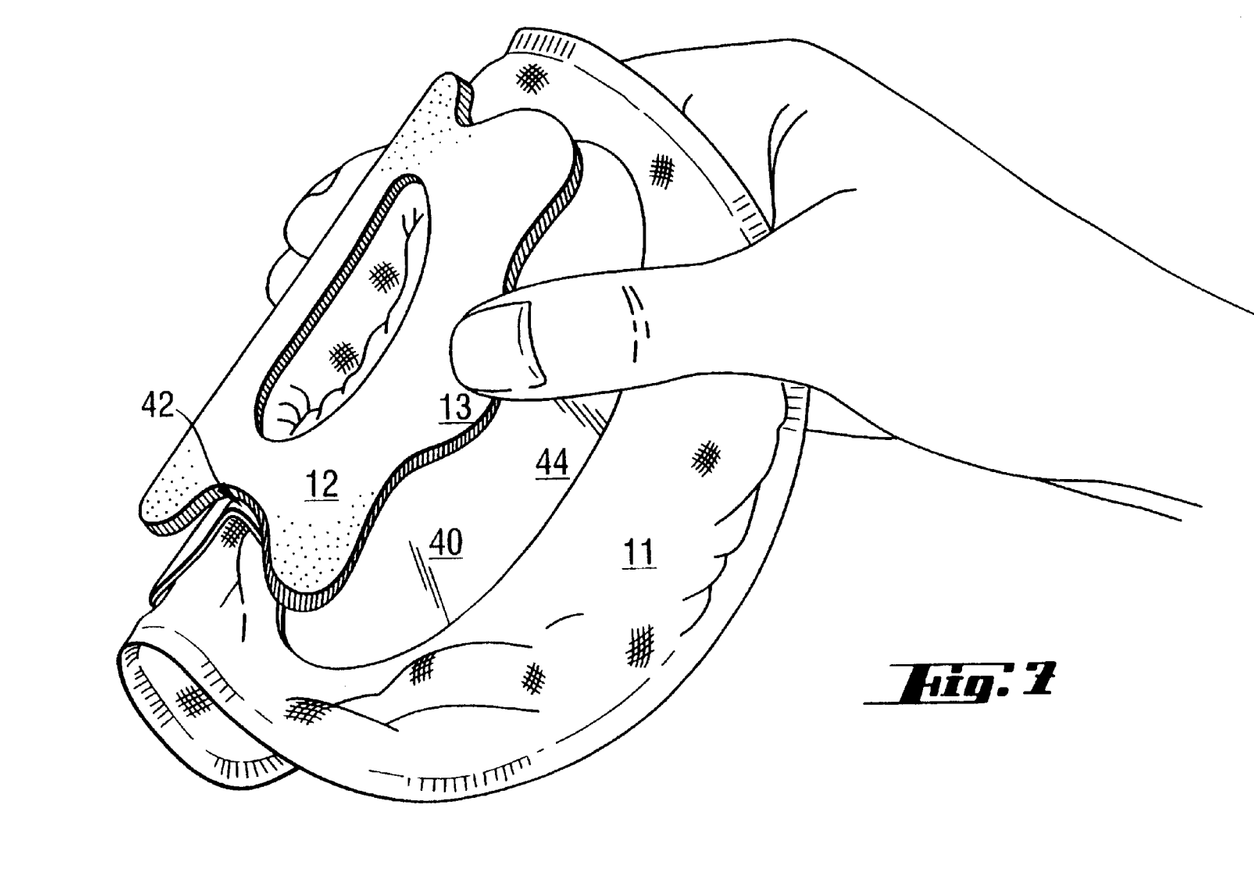
FIG. 7 is a schematic view of the preferred embodiment of the applicator as described in FIG. 6, in combination with a preferred faecal management device.
Figure 8:
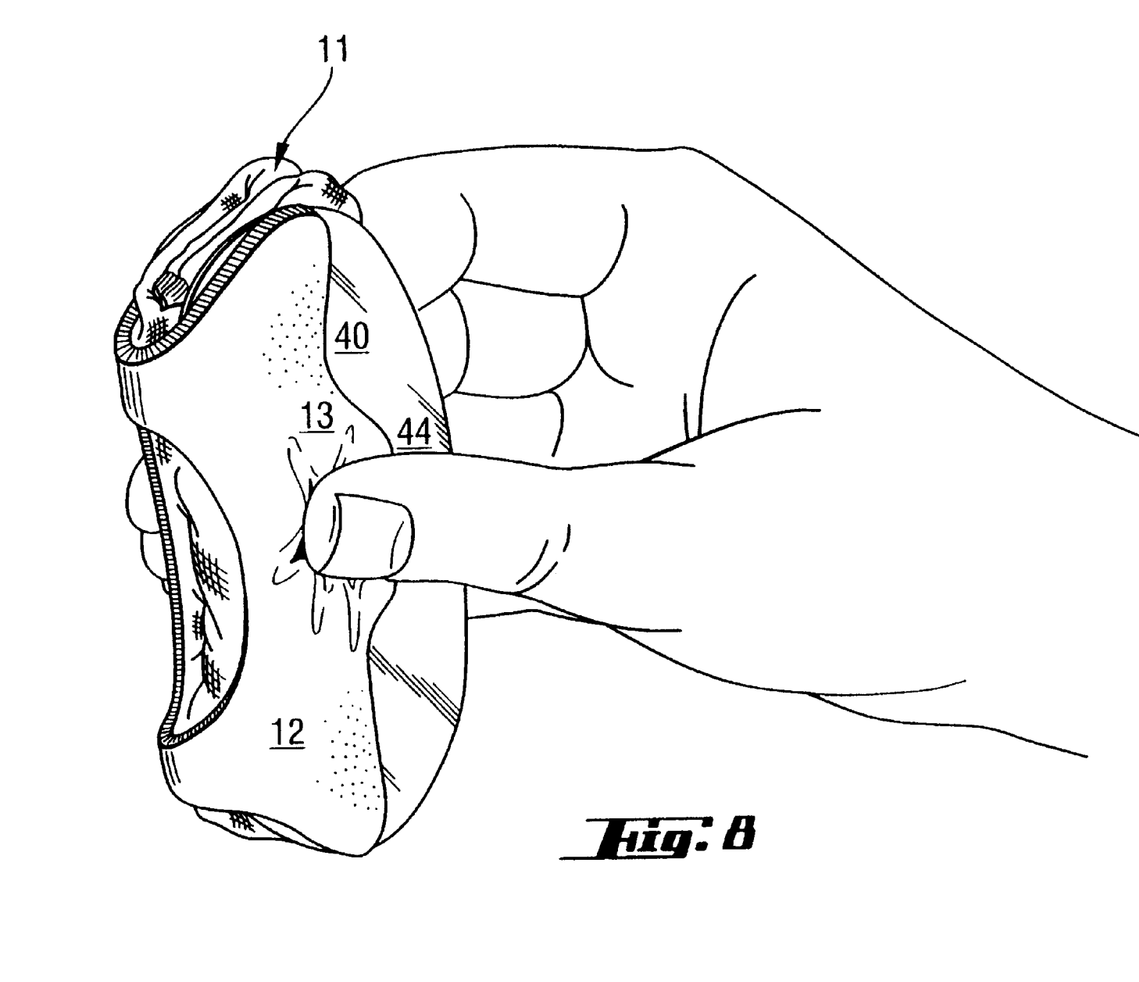
FIG. 8 is a schematic view of the preferred embodiment of the applicator as described in FIG. 6, in combination with a preferred faecal management device, in which the bag of said device is folded.

FIGS. 7 and 8 describe one preferred combination of an applicator (40) and a faecal management device (10) comprising an applicator (40) as depicted in FIG. 6, which comprises two pressure points (42) and a central orifice. Most preferably the bag (11) is folded as described above and illustrated in FIG. 8. The applicator (40) is positioned so, that the central orifice of the applicator (40) and preferably the handling portion (44) enclose portions of the bag (11), preferably portions of the wearer facing portion (16) which are close to the flange (12). If the bag (11) is provided with a neck portion or conduit, the orifice of the applicator (40) will be positioned to enclose these portions. For the positioning of the two pressure points (42) those areas of the wearer facing portion (16) which are relevant will be in contact with the perineal and the coccygeal area of the wearer, in a preferred embodiment projections (28) and (29) are present in these areas. The pressure points (42) of the applicator (40) are brought in registry with the areas of the garment facing portion (17) which are opposite to said areas of the wearer facing portion (16) as can be seen in FIG. 7. The handling portions (44) of the applicator (40) are then adjacent to the placement lobes (13), which are present in a preferred embodiment of the faecal management device (10), as illustrated in FIG. 8. The flange (12) and the applicator (40) are bent along the longitudinal axis, the angle of bending being 135° to 180°, preferably 160° to 180°. The folding of the applicator (40) maintains the folding of the bag (11). A rubber band can be used to ensure the bending of the applicator (40) and the flange (12). The folded applicator (40) provides mechanical and hygienic protection for the faecal management device (10).

Another and even more preferred combination of the applicator (40) and a faecal management device (10) comprises the applicator (40) depicted in FIG. 5. Most preferably the bag (11) is folded as described above. The applicator (40) is positioned in-between the fold of the bag (11) along the longitudinal axis. Thus, the bag (11) covers the portions to either side of the applicator (40) adjacent to the handling portions (44). The central pressure point (42) is positioned to lie in registry with the centre of the aperture (21) of the device (10). The other two pressure points (42) of the applicator (40) are brought in registry with said areas of the garment facing portion (17) and enable the exertion of pressure onto the coccygeal and perineal areas of the wearer. The notches in the applicator (40) depicted in FIG. 5 can be used to hold in place a rubber band. This rubber band covers parts of the flange (12) and of the bag (11). Hence, the rubber band maintains the positioning of the bag (11) relative to the applicator (40) and helps to maintain the folded configuration of the bag (11).

Placing a faecal management device (10) which is provided in combination with an applicator (40) by using the applicator (40) by a person comprises the following handling steps:

a) unpacking of the faecal management device (10) and the applicator (40);
b) holding the device (10), which preferably comprises placement lobes (13), and the applicator (40) by using the placement lobes (13) on the flange (12) and/or using the handling portion (44) of the applicator (40);
c) removing the release means from the adhesive (20) provided on said flange (12), preferably using one hand for the removal of the release means while holding the device (10) and the applicator (40) with the other hand;
d) supporting the placement body position of the wearer, using one hand, e.g. holding up the babies legs, while holding the device (10) and the applicator (40) with the other hand;
e) placing said device (10) in the perianal area of the wearer by using the placement lobes (13) on the flange (12) and/or using the handling portion (44) of the applicator (40);
f) letting said adhesive (20) on said flange (12) attach to the body of the wearer;
g) exerting pressure towards the perineal area of the wearer, the coccygeal area of the wearer or other areas of the wearer to be in contact with the adhesive (20), or a combination thereof, by using the applicator (40), either at the same time or in any sequence;
h) releasing the grasp of the placement lobes (13);
i) separating of the applicator (40) from the device (10) while holding it using the handling portion (44), e.g. by pulling in a direction substantially away from the perianal area of the wearer;
j) unfolding the bag (11) so that it covers the buttocks of the wearer.

Depending on the used embodiment of the present invention and conditions of the placement numerous other handling steps in placing the device (10) using an applicator (40) may also be undertaken, different handling steps may be undertaken or certain of the mentions handling steps may not be involved.

What is claimed is:

1. A method for a caretaker or a wearer for the placement of a faecal management device, comprising two placement lobes, using an applicator to be used for the placement of a faecal management device on a wearer, the applicator comprising a handling portion, said method comprises the steps of:

holding said faecal management device by the placement lobes on the flange and/or the handling portion of the applicator with a first hand;

removing the release means from the adhesive provided on said flange, using a second hand for the removal of the release means while holding said faecal management device and said applicator with said first hand;

supporting the body position of the wearer for placement using the second hand, while holding said faecal management device and said applicator with said first hand;

placing said device in the perianal area of the wearer by using the placement lobes on the flange and/or using said handling portion;

letting said adhesive on said flange attach to the body of the wearer;

exerting pressure towards the perineal area of the wearer, the coccygeal area of the wearer or other areas of the wearer to be in contact with said adhesive, or a combination thereof, by using said applicator, either at the same time or in any sequence;

releasing the grasp of said placement lobes;

separating of said applicator from said faecal management device while holding said applicator using said handling portion;

unfolding said bag so that said bag covers the buttocks of the wearer.

* * * * *